US005436001A

United States Patent [19]

Kramer

[11] Patent Number: 5,436,001

[45] Date of Patent: Jul. 25, 1995

[54] **LIVE, AVIRULENT *SALMONELLA CHOLERAESUIS* VACCINE USED FOR INDUCING AN IMMUNE RESPONSE IN PIGS**

[75] Inventor: Theodore T. Kramer, Ames, Iowa

[73] Assignee: Iowa State University Research Foundation, Ames, Iowa

[21] Appl. No.: 92,877

[22] Filed: Jul. 19, 1993

Related U.S. Application Data

[63] Continuation of Ser. No. 773,429, Oct. 9, 1991, abandoned, which is a continuation-in-part of Ser. No. 607,662, Nov. 1, 1990, abandoned.

[51] Int. Cl.$^6$ .......... A61K 39/12; C12N 1/36; C12N 1/20; C12N 1/00

[52] U.S. Cl. .......... 424/93.4; 435/245; 435/252.1; 435/252.8; 435/879

[58] Field of Search .......... 435/245, 879, 252.1, 435/252.8; 424/93 R, 93 D, 93.4

[56] References Cited

U.S. PATENT DOCUMENTS

| | | | |
|---|---|---|---|
| 3,907,987 | 9/1975 | Wilson | 424/257.1 |
| 3,950,512 | 4/1976 | Emery et al. | 424/89 |
| 3,975,517 | 8/1976 | Wilson | 424/157.1 |
| 4,503,036 | 3/1985 | Girardon et al. | 424/258.1 |
| 4,764,370 | 8/1988 | Fields et al. | 435/879 |

OTHER PUBLICATIONS

Kramer et al., Am. J. Vet. Res., 53 (4) 1992 pp. 444–448.
Sluzewska et al, Pol. Arch. Weter, 18 (2) 1975 (Recd 1976) pp.161–174.
Smith and Jones, "Observations on Experimental Oral Infection with *Salmonella dublin* in Calves and *Salmonella choleraesuis* in Pigs," *J. Pathol. Bacteriol.*, 93:141–156 (1967).
Letter of Jun. 17, 1993 from C. Wray, Central Veterinary Laboratory, New Haw, Addlestone, Surrey, United Kingdom to Professor T. T. Kramer, Iowa State University, Ames, Iowa with two enclosures.
Lawson & Dow, "Experimental Vaccination of Pigs with Avirulent Rough Strains of *Salmonella cholerae suis*," *Brit. Vet. J.*, 121:521–531 (1965).
Scholl and Grunert, "Suisaloral Dessau–Ein Salmonella–cholerae–suis–lebendimpf–stoff zur oralen, parenteralen und Kombinierten Anwendung," *Arch. Exper. Vet. Med.*, (leipzig), 34:91–97 (1980).
Turfano et al., *Microbial Pathogenesis*, 7:337–346 (1989).
Gulig, *Microbial Pathogenesis*, 8:3–11 (1990).
Buchmeier et al. *Infection and Immunity*, 57:1–7 (1989).
Fields et al., *Science*, 243:1059–1062 (1989).
Buchmeier et al., *Science*, 248:730–732 (1990).
Griffith et al., *Am. J. Vet. Res.*, 45:1342–1348 (1984).
Fields et al., *Proc. Natl. Acad. Sci.*, 83:5189–5193 (1986).
Maurelli, *Microbial Pathogenesis*, 7:1–10 (1989).
Groisman et al., *Proc. Natl. Acad. Sci.*, 86:7077–7081 (1989).
Finlay et al., *J. of NIH Res.*, 1:84–87 (1989).
Dougan et al., *Adv. Ve. Rad. Vet. Sci. and Comp. Med.*, 33:271–300 (1989).

(List continued on next page.)

*Primary Examiner*—Marian C. Knode
*Assistant Examiner*—Susan M. Dadio
*Attorney, Agent, or Firm*—Dickstein, Shapiro & Morin

[57] ABSTRACT

Disclosed herein are methods for attenuating virulent gram negative bacteria to produce avirulent bacteria. The methods comprise passaging the wild-type bacteria through phagocytic cells, such as macrophages or polymorphonuclear leukocytes, or through lysosomes derived from such cells, a sufficient number of times until the bacteria become avirulent to the animal host. The bacteria are preferably from the family Enterobacteracea and most preferably from the genus Salmonellae. The invention further comprises the avirulent bacteria produced by the methods, pure cultures of such bacteria, and methods of using the bacteria, preferably in a vaccine for administration to an animal host to induce an immune response to the wild-type gram negative bacteria in the host.

4 Claims, 3 Drawing Sheets

OTHER PUBLICATIONS

Roof et al. *Vet. Immunology & Immunopathology,* 23 (3–4), 1989, pp. 365–376 (Biosis Abstract #89083449).

Griffith et al. *Vet. Immunology & Immunopathology,* 4, (1983) pp. 593–601.

Mungar et al. *Abstracts of the Annual Meeting,* 1983, (E98) p. 92.

Kramer et al. *Am. J. Vet. Res.,* vol. 48, No. 7, Jul. 1987, pp. 1072–1076.

Finlay et al. *J. Cell. Biol.,* 107:221–230 (1988).

Roof et al., "Characterization of a *Salmonella cholerae-suis,* Isolate After Repeated Neutrophil Exposure," *Amer. J. Vet. Res.,* 53:1328–1332 (1992).

Kramer et al., "Safety and Efficacy of an Attenuated Strain of *Salmonella choleraesius* for Vaccination of Swine," *Amer. J. Vet. Res.,* 53:444–448 (1992).

Kramer and Wood, "Local and Systemic Immunity to *Salmonella Choleraesius,* Proceedings of the 91st Annual Meeting of the United States Animal Health Assn.," Salt Lake City, Utah 1987.

Smith, "The Immunization of Mice, Calves, and Pigs against *Salmonella dublin* and *Salmonella cholera-suis* Infections, " *J. Hyg. Camb.,* 63:117–135 (1965).

Taira et al., *Microbial Pathogenesis,* 7:165–173 (1989).

Benjamin et al., *Infection and Immunity,* 51:872–878 (1986).

Nnalue et al., *Infection and Immunity,* 55:955–962 (1987).

Nnalue, "Mice Vaccinated With a Non–Virulent, Aromatic–Dependent Mutant of *Salmonella Cholerae-suis* Die From Challenge With Its Virulent Parent But Survive Challenge With *Salmonella typhimurium, J. Med Microbiol.*"31:225–233 (1990).

Quaife, "Unlocking its Deadly Grip", *Swine Practitioner,* pp. 4–7, Feb. 1992.

Edwards et al., *Identification of Enterobacteriaceae (3rd edition), Burgess Publishing Co. Minneapolis, Minn., p. 154.*

Supplementary European Search Report, Appln. No. EP 92 90 0047, Mar. 10, 1994.

File Server STN Karlsruhe, File Medline Abstract No. 83159793 & Infect. Immun. (1983 Feb.) 39 (2) 779–84 Collins et al. "Bactericidal Activity of Alveqlar and Peritoneal Macrophages Exposed in Vitro to Three Strains of Pasteurella Multocida" (Abstract).

File Server STN Karlisruhe, File Biosis Abstract No. 88:71320 & J. Exp. Med. 166(5). 1987. 1310–1328 Horwitz: "Characterization of Avirulent Mutant Legionella–Pneumophila That Survive But Do Not Multiply Within Human Monocytes" (Abstract).

LIVE, AVIRULENT *SALMONELLA CHOLERAESUIS* VACCINE USED FOR INDUCING AN IMMUNE RESPONSE IN PIGS

This application is a continuation of Ser. No. 07/773,429 filed Oct. 9, 1991, now abandoned, which is a continuation-in-part of application Ser. No. 07/607,662 filed Nov. 1, 1990, now abandoned.

FIELD OF THE INVENTION

This invention relates generally to a bacterial attenuation method and to vaccine production. Specifically, it relates to a method of attenuating gram negative bacteria to produce avirulent bacteria that are useful in vaccines for humans and animals. One such strain has been field tested and found to have effectively prevented salmonellosis in swine and pigs with no reversion to virulence.

BACKGROUND OF THE INVENTION

Gram negative bacteria cause a wide variety of diseases in humans and animals. These include plague, caused by *Yersinia pestis,* typhoid fever, caused by *Salmonella typhi,* gonorrhea, caused by *Neisseria qonorrhoeae,* dysentery, caused by *Shigella dysenteriae,* gastroenteritis, commonly caused by *Salmonella typhimurium, Escherichia coli,* and *Campylobacter jejuni,* bacterial sepsis, caused primarily by *Escherichia coli, pseudomonas aeruginosa,* and *Klebsiella pneumoniae,* and septicemic diseases in cattle and pigs, caused by *Salmonella dublin* and *Salmonella choleraesuis,* respectively.

Humans and animals have evolved many defenses to infection by gram negative bacteria. One of the first lines of defense are the body's phagocytic cells. These cells engulf invading microorganisms and kill them by various methods, such as the release of proteolytic enzymes and oxygen radicals.

Unfortunately, many types of bacteria have evolved means to inhibit or resist the many microbicidal substances in phagocytic cells, thereby allowing them to survive within the cells. Such facultative intracellular pathogens are a clinically important group of bacteria. They include bacteria from the genera Salmonelia, Yersinia, Shigella, and Neisseria.

Because the intraphagocytic environment is so hostile to bacteria, it seems reasonable to assume that the selection of bacteria from within phagocytes would follow the Darwinian principle of survival of the fittest. Current reports indicate that, in order to survive in phagocytes, Salmonellae must possess virulence attributes, such as plasmids, porins, and other outer membrane proteins related to virulence. See Taira, et al., *Microbial Pathogenesis,* 7:165–173 (1989), Tufano, et al., *Microbial Pathogenesis,* 7:337–346 (1989), and Gulig, *Microbial Pathogenesis,* 8:3–11 (1990), all of which are incorporated herein by reference. It has also been reported that mutants unable to survive in macrophages have lost immunogenicity and virulence when compared to their parental strains. See Buchmeier, et al., *Infection and Immunity,* 57:1–7 (1989), Fields, et al., *Science,* 243:1059–1062 (1989), and Buchmeier, et al., *Science,* 248:730–732 (1990), all of which are incorporated herein by reference. Therefore, the reasonable expectation would be that Salmonellae able to survive in phagocytic cells would possess optimal virulence properties.

Surprisingly, the inventor has discovered the opposite result to that expected. Salmonellae that survived serial passages through live phagocytic cells or their lysosomal products exhibited decreased virulence and, after a sufficient number of passages, became avirulent. The avirulent bacteria still produced an immunogenic response when innoculated into an animal host, thereby providing the basis for vaccines against gram negative bacteria.

Such vaccines would be highly desirable because such bacteria, particularly the faculatative intracellular pathogens, are often able to evade the body's defense mechanisms. A vaccine would prepare and enhance the defense mechanisms prior to significant invasion by the bacteria against which the vaccine is directed. Live, avirulent bacteria, as opposed to killed bacteria or inactivated toxins, are particularly desirable as vaccines because they usually provide a broader immune system response.

SUMMARY OF THE INVENTION

It is an object of the invention to provide methods of attenuating gram negative bacteria that are virulent to an animal host, thereby producing avirulent gram negative bacteria.

A further object of the invention is to provide avirulent, gram negative bacteria.

A still further object of the invention is to provide a method and vaccine for inducing an immune response in an animal host to gram negative bacteria.

Another object of the invention is to provide a method and vaccine for protecting an animal host against gram negative bacteria.

Additional objects and advantages of the invention will be set forth in part in the description that follows, and in part will be obvious from the description, or may be learned by the practice of the invention. The objects and advantages of the invention will be attained by means of the instrumentalities and combinations particularly pointed out in the appended claims.

To achieve the objects and in accordance with the purpose of the invention, as embodied and broadly described herein, the present invention provides methods of attenuating gram negative bacteria that are virulent to an animal host. In the preferred embodiment, the virulent, wild-type gram negative bacteria are passaged through phagocytic cells a sufficient number of times until the bacteria become avirulent to the host but are still immunogenic. Preferably, the phagocytic cells are polymorphonuclear leukocytes (PMNLs). In an alternative embodiment, the wild-type gram negative bacteria are passaged through cultures of lysosomes obtained from phagocytic cells a sufficient number of times until the bacteria become avirulent to the host but are still immunogenic. Preferably, the lysosomes are obtained from PMNLs.

The invention further comprises avirulent gram negative bacteria produced by the methods of attenuation described herein. Preferably, the virulent gram negative bacteria are selected from the family Enterobacteracea. Most preferably, the bacteria are selected from the genus Salmonella.

The invention further comprises an avirulent strain of *Salmonella choleraesius.* The strain metabolizes both glycerol and d-xylose, exhibits increased resistance to being killed by neutrophils and hydrogen peroxide as compared to wild-type *Salmonella choleraesuis* strains, and is noninvasive to Vero cells.

The invention further comprises a vaccine and method for inducing an immune response to gram negative bacteria in an animal host. A vaccine comprising an immunologically effective amount of the avirulent bacteria of the invention in a pharmaceutically acceptable carrier is administered to the animal host.

Other features of the invention will be apparent from the Detailed Description and the figures.

DETAILED DESCRIPTION OF THE INVENTION

Figure 1:
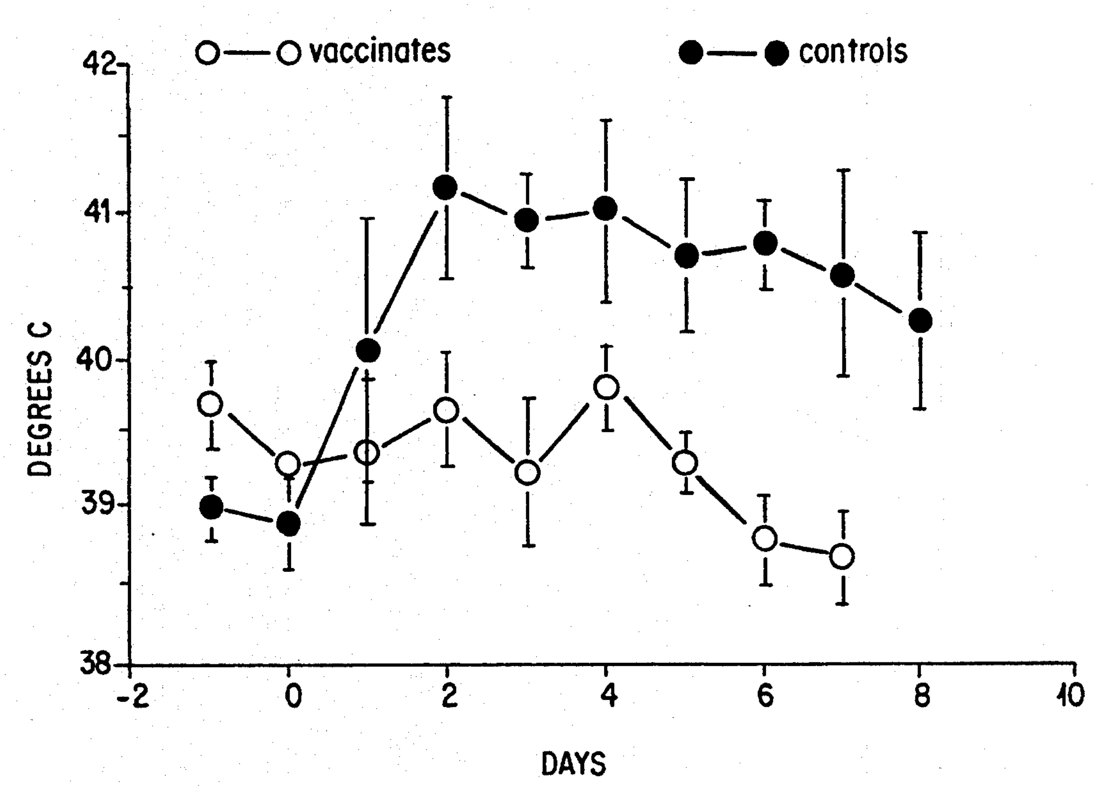
FIG. 1 is a graphic representation of the daily rectal temperatures of 5 pigs given neutrophil adapted *S. choleraesuis* strain 54 and 5 pigs given the virulent parent strain 38 per os.

Reference will now be made in detail to the presently preferred embodiments of the invention, which, together with the following examples, serve to explain the principles of the invention.

The invention relates to methods for attenuating virulent, wild-type gram negative bacteria, to the resulting attenuated or avirulent bacteria, and to vaccines containing such bacteria. As used herein, the term "virulent" pertains to bacteria that are capable of invading the tissues of an animal host and causing disease or other pathologic effects. Virulence is measured by severity of disease and can be quantitated by the median lethal dose ($LD_{50}$) in experimental animals, the numbers of organs (generally spleen or liver) colonized by the bacteria, and the colony forming units (CFUs) from the infected organs. As used herein, the term "attenuated" refers to the weakening or decreasing of the virulence of the wild-type bacteria. As used herein, the term "avirulent" refers to previously virulent bacteria that have been attenuated to a sufficient degree that they are no longer virulent to their natural animal host. Thus, their administration to the animal host would not cause disease. Generally, such avirulence can be shown by a decrease in the $LD_{50}$, the numbers of colonized organs, or the number of CFUs by a factor of 10, preferably by a factor of 100, and most preferably by a factor of 1000.

The methods of the invention are directed to attenuating gram negative bacteria that are virulent to an animal host to a sufficient degree to produce gram negative bacteria that are avirulent to the host. In the preferred embodiment, the method comprises serially passaging the virulent, wild-type gram negative bacteria through phagocytic cells a sufficient number of times until the bacteria are rendered avirulent to the animal host while still being immunogenic. In particular, the bacteria are mixed and incubated with the phagocytic cells, under conditions conducive to the maintenance and growth of the bacteria, for a sufficient period of time for most of the bacteria to be phagocytized by the cells. The amount of bacteria and cells and the time, temperature, and other conditions for passaging will be known to those skilled in the art or easily determinable without undue experimentation, given the teachings contained herein. Preferably, the bacteria are mixed with the cells in a ratio from about 100 to 1 to about 5 to 1 at a temperature of about 35° C. to 40°0 C. for approximately 30 to 60 minutes. Most preferably, the ratio of bacteria to cells is approximately 10:1, the temperature is about 37° C., and the time of incubation is approximately 45 minutes. Phagocytosis of the bacteria is facilitated by the addition of specific antibody in a sub-agglutinating concentration (usually diluted 1:100 to 1:200). The reactants are preferably suspended in a tissue culture medium (M199) containing 10% fetal calf serum.

The unphagocyted bacteria are then separated from the phagocytic cells. Preferably, this is done by killing the unphagocytized bacteria by contacting the mixture with an antibiotic agent that does not harm the phagocytic cells. Preferred antibiotics include gentamicin and kanamycin. The amount or concentration of antibiotic and the time it is contacted with the mixture will be known to those skilled in the art or easily determined without undue experimentation, given the teachings contained herein. Preferably, the concentration of antibiotic is from about 25 to about 150 ug (micrograms), and the contact time is from about 15 to about 45 minutes. Most preferably, the concentration is about 100 ug, and the contact time is about 30 minutes.

The phagocytized bacteria are recovered from the phagocytic cells by disrupting the cells and separating the bacteria from the cellular debris. The phagocytic cells can be disrupted mechanically, by osmotic lysis, or chemically. Preferably, disruption is by exposure to a 0.2% solution of saponin for about 10 to 30 seconds. The period of time from the beginning of the passaging step to the beginning of the recovery step is approximately from 60 to 120 minutes.

The number of serial passages necessary for obtaining avirulent bacteria will vary somewhat, depending upon the nature of the starting bacteria, the nature of the phagocytic cells, and the type of animal host, but the number will be readily determinable without undue experimentation by persons skilled in the art, given the teachings contained herein. Generally, the number of passages will be at least 5, preferably 8, and most preferably 12.

As mentioned above, the bacteria are passaged through phagocytic cells. Such cells include macrophages and microphages. Of the microphages, PMNLs (also called neutrophils) are the ones that engulf bacteria. Therefore, they are the only microphages that should be deemed to come within the scope of the term phagocytic cell as used herein. Moreover, PMNLs are the preferred cells for use in this method of the invention.

It is preferred that the phagocytic cells are free of any bacteria before passaging is initiated, and it is highly preferred that the cells be free of the same type of bacterium as that bacterium which is to be passaged through the cells. Such freedom from contamination can be determined by techniques known in the art.

In an alternative embodiment of the invention, the method for attenuating the bacteria comprises passage through lysosomes instead of phagocytic cells. The lysosomes are organelles of the phagocytic cells that contain most, if not all, of the many bactericidal compounds that such cells use to destroy foreign microorganisms.

The lysosomes are obtained from phagocytic cells by known techniques. Preferably, the phagocytic cells are PMNLs. The wild-type, virulent gram negative bacteria are then passaged through mixtures of such lysosomes for a sufficient number of times until the bacteria become avirulent to the animal host while still being immunogenic. The passaging comprises mixing and incubating the bacteria with the lysosomes, under conditions conducive to the growth of the bacteria, and then separating the bacteria from them using known techniques, such as centrifugation. Repeated serial passaging results in the eventual recovery of avirulent bacteria. Fresh lysosomes are used for each passage. Preferably, the bacteria are grown by culturing in a bacterial growth medium after each recovery from the lysosomes and prior to the next passage through the fresh lysosomes.

The relative amounts of bacteria and lysosomes, the times the bacteria are in contact with the lysosomes and the culture medium, and the temperature and other conditions for passaging will depend primarily upon the particular type of gram negative bacteria and the particular animal host. However, these and other conditions will be known to those skilled in the art or easily determinable without undue experimentation, given the teachings contained herein. Preferably, the bacteria are mixed with the lysosomes in a volume ratio from about 1 to 5 to about 1 to 20 at a temperature of about 37° C. to about 42° C. for approximately 30 to 60 minutes. Most preferably, the ratio of bacteria to lysosomes is approximately 1 to 10, the temperature is about 37° C., and the mixing time is approximately 30 to 45 minutes.

The number of serial passages necessary for obtaining avirulent bacteria will vary somewhat, depending upon the nature of the starting bacteria, the nature of the phagocytic cell from which the lysosomes are obtained, and the type of animal host, but the number will be readily determinable without undue experimentation by persons skilled in the art, given the teachings contained herein. Generally, the number of passages will be from about 5–15, preferably about 13.

As mentioned above, the method of the invention may be applied to any gram negative bacteria. Such bacteria have similar virulence characteristics and invasion strategies. They also have very similar outer membrane structures, including pill and adhesion proteins. The preferred animal hosts are any animals that may be infected by such bacteria. These include, but are not limited to, humans and other primates or mammals, cattle, swine, birds, and fish.

Within the category of gram negative bacteria, a preferred subcategory are bacteria from the family Enterobacteriacea. Many types of bacteria from this family infect humans and many animals. Particularly important within this family are Salmonellae Shigellae, Klebsiellae, Eschericheriae, and Yersiniae. These bacteria are particularly troublesome to humans and commercially important animals, such as cattle and swine. Particularly important species within these genera include *S. typhi, S. choleraesuis, S. dublin, S. enteritidis, S. typhimurium, Shigella. dysenteriae, K. pneumoniae, E. coli,* and *Y. pestis.*

Another important subcategory of gram negative bacteria are the facultative intracellular pathogens. These include the genera Neisseria and Brucellae and the previously mentioned genera Salmonella, Yersinia, and Shiqella. Within the first two genera, particularly important species include *N. gonorrhoeae* and *B. abortus.*

Still other important gram negative bacteria are those from the genera Pseudomonas and Haemophius particularly the species *P. aeruginoa,* H. spp, and *H. influenzae.*

The attenuated or avirulent gram negative bacteria produced by the methods of the invention are encompassed within the invention. Preferably, such bacteria are in pure culture, and, accordingly, the invention encompasses compositions of matter comprising such pure cultures. As used herein, the term "pure culture" means a composition comprising the bacteria in a culture medium, wherein the mixture is free of other microorganisms.

For both methods of the invention, the preferred bacteria are from the genus Salmonellae. Within this genus, the preferred species are *S. choleraesuis* and *S. dublin,* which infect pigs and cattle, respectively, and *S. enteritidis,* which infects many host species, including humans and birds. The most preferred starting bacterial variety is *S. choleraesuis* var. *Kunzendorf* strain 38, which gives rise to the avirulent strain *S. choleraesuis* var. *Kunzendorf* strain 38 PMNa. Strain 38 is preferably used because of its virulence and ability to ferment glycerol (+) which can then be used as a marker for recovery. Both the parent and vaccine strains ferment glycerol which thus distinguishes them from other *S. choleraesuis* strains.

*S. choleraesuis* var. *Kunzendorf* strain 38 PMNa is distinguished from its wild-type parent by the absence of the virulence plasmid exhibited by the parent and by being able to grow on a medium containing d-xylose, which it metabolizes. Additionally, it exhibits an overall increased resistance to PMNL killing and to killing by hydrogen peroxide, and it was non-invasive in a Vero cell assay. A pure culture of this avirulent strain was deposited under the Budapest Treaty on Oct. 29, 1990 in the permanent collection of the American Type Culture Collection (ATCC), 12301 Parklawn Drive, Rockville, Md. U.S.A. 20852 and assigned accession number 55105.

Given the teachings contained herein and this particular strain, persons skilled in the art can use known techniques to obtain mutants and derivatives that still have the utility as immunogens in antimicrobial vaccines as does the parent avirulent strain (Kunzendorf strain 38 PMNa). For example, such mutants or derivatives may have different nutritional requirements, different resistance to neutrophil killing and killing by hydrogen peroxide or may exhibit different degrees of non-invasiveness in Vero cell assays. However, as long as they are derived from the strain and have immunogenic activity, they are within the scope of this invention.

The avirulent bacteria of the invention are expected to have utility as immunogens in antimicrobial vaccines for animals, including birds, fish, cattle, swine, horses, mammals and primates in general, and humans. Such vaccines can be prepared by techniques known to those skilled in the art, given the teachings contained herein. Such a vaccine would comprise an immunologically effective amount of the avirulent bacteria of the invention in a pharmaceutically acceptable carrier. The vaccine could be administered in one or more doses. An immunologically effective amount is determinable by means known in the art without undue experimentation, given the teachings contained herein. The amount of avirulent bacteria should be sufficient to stimulate an immune response in disease-susceptible animals while still being avirulent. This will depend upon the particular animal, bacteria, and disease involved. The recommended dose to be administered to the susceptible animal is preferably about $10^7$–$10^9$ bacteria/Kg of body weight and most preferably about $10^8$ bacteria/Kg of body weight. The carriers are known to those skilled in the art and include stabilizers and diluents. Such a vaccine may also contain an appropriate adjuvant. The vaccine preparations may also be desiccated, for example, by freeze drying for storage purposes or for subsequent formulation into liquid vaccines.

Accordingly, the invention also comprises a method for inducing an immune response to virulent, wild-type gram negative bacteria in an animal host for the purpose of protecting the host from such bacteria. The method comprises administering an immunologically effective amount of the avirulent gram negative bacteria of the invention to the host and, preferably, administering the vaccine of the invention to the host.

The vaccines may be administered to animals by various routes, including oral, intramuscular, subcutaneous, and intranasal. The preferred route of administration is oral.

In the preferred embodiment of the invention, the vaccine comprises avirulent *S. choleraesis* produced by the method of the invention. It would contain about $10^8$ bacteria in sterile water per kilogram of body weight. It would be administered orally in a duodenal capsule.

The avirulent bacteria produced by the method of the invention are also useful as reagents for scientific research on the properties of pathogenicity, virulence, and infectivity of gram negative bacteria, as well as host defense mechanisms. A composition in accordance with the present invention useful as an investigational reagent contains an amount of avirulent bacteria effective to provide the information or analysis sought. The determination of the amount necessary to accomplish a particular research goal depends upon the specific type of investigation involved and is readily within the routine skill of one engaged in such research.

It is to be understood that the application of the teachings of the present invention to a specific problem or environment will be within the capabilities of one having ordinary skill in the art in light of the teachings contained herein. Examples of the products of the present invention and processes for their use appear in the following examples.

EXAMPLE 1

Selection for Avirulence of Salmonellae in Polymorphonuclear Leukocytes

The fate of bacteria that survive in polymorphonuclear leukocytes (PMNL)s and the changes that occur in the surviving bacterial population have not been extensively documented. In order to detect the effect of PMNL residency on virulence properties of Salmonellae, Salmonellae were serially recovered from PMNLs. Compared to the source strains, PMNL-adapted *S. choleraesuis, S. dublin,* and *S. enteritidis* invaded tissue culture cells, such as VERO cells, about 10 times less effectively than the source strain, and became totally or almost totally avirulent for mice and pigs. Virulence was measured by $LD_{50}$, numbers of spleens colonized with Salmonellae, and colony forming units (CFU) from infected spleens. Salmonellae adapted to PML were immunogenic.

Materials and Methods

Selection of *S. choleraesuis* (SC.) and other Salmonellae 38 from porcine PMNLs. Scs 38 was grown overnight on trypticase soy agar. A single colony was suspended in phosphate buffered saline solution, and the solution adjusted to a concentration of $2\times10^8$ CFUs. Porcine PMNLs were isolated from venous blood by lysis of erythrocytes and centrifugation in a Ficol-Hypaque gradient density to separate the PMNLs from lymphocytes. The PMNL suspension was adjusted to a $5\times10^7$ cells/ml in phosphate buffered saline and resuspended in medium M199 containing 10% fetal calf serum. Equal volumes of Scs 38 and PMNLs were incubated for 45 min at 37° C. After centrifugation at 1600 rpm, the PMNL pellet was resuspended in PBS containing 100 ug gentamicin and 100 ug kanamycin and incubated for 30 min. Following centrifugation, the PMNL supernatant was inoculated on MacConkey agar and incubated for 48 hours. The pellet was suspended in a 0.1% solution of SDS (or preferably in 0.2% saponin) in PBS to disrupt PMNLs, and immediately cultured on MacConkey agar. It was important to insure that all Scs 38 recovered after this procedure originated from surviving phagocytosed bacteria, and did not include Scs 38 that somehow survived on the surface of PMNLs or in the antibiotic medium. Only treatments with no growth in the supernatant fraction after 48 hours incubation were therefore considered successful passages of Scs in PMNL. Certain strains were subjected to multiple PMNL exposure. Thus, following culture on MacConkey agar, after exposure to PMNLs as described above, individual colonies were selected and resuspended to $2\times10^8$ colony forming units (cfu)/ml. The above-described PMNL exposure procedure was then repeated for varying number of times, i.e., five and seven. Following multiple passage completion, a single glycerol (+) clone was selected and designated.

Selection of *S. choleraesuis* (Scs) and other Salmonellae 38 from porcine Lysosomes. Lysosomes were extracted from PMNL by freeze-fracturing PMNLs after their purification and centrifuging the debris at 1,600 g for 20 min. The supernatant was concentrated through an Amicon membrane and sterile filtered through a Millipore membrane filter. Equal volumes of Salmonellae were alternatively incubated for periods of 30 min in the lysosome extract and trypticase soy broth (30 min in lysosome extract followed by 30 min in trypticase soy broth etc). Only the lysosome incubation was counted as a cycle. That is, a 13× extraction consisted of 13 lysosomal incubation and 13 trypticase soy broth incubation periods.

Mouse inoculations. Swiss Webster mice were inoculated with specified numbers of Salmonellae into the left footpad by subcutaneous injection, using a tuberculin syringe fitted with a 26" needle. The injection volume was 80 ul. The mice were sacrificed, and the spleens were harvested, homogenized, and cultured for Salmonellae using a microdilution technique. Data were pooled from several experiments. Lethal dose 50's ($LD_{50}$) were computed according to the formula of Reed and Muench.

Pig inoculations. Pigs were infected with Scs 38 and its PMN-adapted derivative by oral gavage, after 24-hour fasting. The inoculums were suspended in phosphate buffered saline to neutralize stomach acid.

Results and Discussion

*Salmonella choleraesuis* var *Kunzendorf* strain 38 (Scs 38) was chosen for the experiments because of its strong and well-defined virulence properties. See Griffith, et al., *Am. J. Vet. Res.,* 45:1342–1348 (1984) and Finlay, et al., *J. Cell. Biol.*, 107:221–230 (1988), both of which are incorporated herein by reference. The virulence of Salmonellae serially exposed to live porcine PMNLs or their lysosomal products was examined. Virulence for mice decreased with subsequent exposures of Salmonellae to PMNLs or lysosomes (Table 1). Virulence, judged by $LD_{50}$ and ability to invade and grow in the mouse spleen, was gradually decreased and ultimately abolished when mice were infected with *S. choleraesuis* subjected to serial passages through pig PMNLs (Table 1). Similarly, virulence was abolished when *S. choleraesuis* was exposed serially 13× to PMNL lysosomal extracts (Table 1). When *S. choleraesuis* was fed by gavage to pigs, the natural hosts of *S. choleraesuis*, the PMNL-adapted Salmonellae caused no clinical ill effects, whereas the wild source type caused high fever, anorexia, and diarrhea (data not shown). Death and multiple organ infections with high numbers of Salmonellae occurred in the group of pigs that received the wild type, whereas no death occurred, and organ infection was minimal, in pigs receiving PMNL-adapted Salmonellae (Table 3).

The investigation was then extended to *S. dublin* and *S. enteritidis*. *S. dublin* is a cattle-adapted pathogen, causing severe enteritis and septicemia, primarily in dairy calves. *Salmonella enteritidis* is not adopted to a particular host. It occurs commonly in eggs and poultry and is the cause of most current human Salmonella food poisonings in the U.S.A. The $LD_{50}$ of the PMNL-adapted *S. choleraesuis*, *S. dublin*, and *S. enteritidis* was at least 3 logs higher than the $LD_{50}$ of the respective source strains (Table 2). The number of spleens infected, and the number of Salmonellae per infected spleen, was considerably lower in groups of mice that were infected with the PMNL-adapted respective Salmonellae (Table 4). In addition to loss of virulence, PMNL selection of Salmonellae resulted in strong protective immunity (Table 5). Immunity was dose-dependent, and was accompanied by the persistence in low numbers of the immunizing PMNL-adapted *S. choleraesuis* (Table 5).

*Salmonella choleraesuis* and *S. dublin* cause in their host species a septicemic disease not unlike human typhoid fever. The role of PMNLs is therefore particularly important in host defenses to these diseases, to prevent the systemic spread of salmonella infection. The above observations raise the possibility that PMNLs are "the first line of defense" not only because of their microbicidal role, but also because they select less virulent lineages from a heterogeneous infecting population of bacteria. The mechanism of the attenuated virulence is not known.

TABLE 1

Selection of *S. choleraesuis* (Scs) 38 from porcine PMNL. Data were pooled from 3 experiments.

| Inocula: | Dose | No Mice | Killed days pi | No Dead | No spleens infected | $Log_{10}$ Scs/spleen |
|---|---|---|---|---|---|---|
| | Virulent source strain: *S. choleraesuis* 38 | | | | | |
| Scs 38 | $5.0 \times 10^1$ | 8 | 8 | 0 | 5/8 | 7.74 ± 1.12 |
| Scs 38 | $1.6–5.0 \times 10^1$ | 19 | 14 | 3 | 18/19 | 6.17 ± 0.65 |
| Scs 38 | $1.6–2.6 \times 10^2$ | 26 | 8 | 6 | 23/26 | 6.10 ± 0.92 |
| Scs 38 | $1.6 \times 10^2$ | 9 | 14 | 1 | 9/9 | 4.02 ± 0.16 |
| Scs 38 | $1.6 \times 10^3$ | 10 | 8 | 4 | 10/10 | 6.09 ± 0.40 |
| | Scs 38 1× adapted to porcine PMNLs | | | | | |
| Scs 38 | $4.6 \times 10^2$ | 8 | 8 | 0 | 3/8 | 5.22 ± 0.52 |
| Scs 38 | $4.6 \times 10^2$ | 9 | 14 | 0 | 3/9 | 5.23 ± 0.18 |
| | Scs 38 5× adapted to porcine PMNLs | | | | | |
| Scs 38 | $4.7–6.4 \times 10^1$ | 16 | 8 | 0 | 1/16 | 0.40 |
| Scs 38 | $4.7–6.4 \times 10^1$ | 17 | 14 | 0 | 2/17 | 0.20 ± 0.19 |
| | Scs 38 7× adapted to porcine PMNLs | | | | | |
| Scs 38 | $4.3 \times 10^3$ | 10 | 8 | 0 | 0/10 | 0.00 |
| Scs 38 | $4.3 \times 10^3$ | 10 | 14 | 0 | 0/10 | 0.00 |
| | Scs 38 13× isolated from porcine neutrophil lysosomes | | | | | |
| Scs 38 | $2.8 \times 10^1$ | 8 | 8 | 0 | 0/8 | 0.00 |
| Scs 38 | $2.8 \times 10^1$ | 8 | 14 | 0 | 0/8 | 0.00 |
| Scs 38 | $6.5 \times 10^2$ | 8 | 8 | 0 | 1/10 | 3.00 |
| Scs 38 | $2.5 \times 10^3$ | 5 | 15 | 0 | 0/5 | 0.00 |
| Scs 38 | $2.5 \times 10^4$ | 5 | 15 | 0 | 0/5 | 0.00 |
| Scs 38 | $2.5 \times 10^5$ | 5 | 15 | 0 | 0/5 | 0.00 |

TABLE 2

Lethal dose 50 ($LD_{50}$) of Salmonellae and their PMNL adapted derivatives. Adaptation of Salmonellae to PMNLs was described in Table 1. Groups of 5 mice each were inoculated with tenfold increments of Salmonellae from $10^1$ to $10^5$ in the left footpad in a volume of 80 uL. Surviving mice were sacrificed 10 days after inoculation, and $LD_{50}$ calculated by the method of Reed and Muench.

| Salmonellae | $LD_{50}$ wild | $LD_{50}$ PMNL adapted |
|---|---|---|
| *S. choleraesuis* str 38 | $1.0 \times 10^{2.84}$ | $>2.1 \times 10^5$ |
| *S. dublin* str 127 | $1.9 \times 10^{2.33}$ | $>1.5 \times 10^5$ |
| *S. enteritidis* str 129 | $1.9 \times 10^{2.66}$ | $>2.1 \times 10^5$ |

TABLE 3

Organ invasion of wild-type *S. choleraesuis* strain 38 (Scs 38) and its PMNL-adapted derivative (Scs 38 7× PMNL) in pigs. Pigs were fed respective cultures by gavage. All surviving pigs were euthanized two weeks after infection and selected organs were cultured from tenfold dilutions of organ suspensions. The numbers denote $log_{10}$ of colony forming units. A single colony from the 1:10 (lowest) dilution was noted by "+".

| | Pigs | | | | | | | | | |
|---|---|---|---|---|---|---|---|---|---|---|
| | 1 | 2 | 3 | 4 | 5 | 6 | 7 | 8 | 9 | 10 |
| Inocula | Scs 38 7× PMNL $3.7 \times 10^9$ | | | | | | Scs 38 $3.2 \times 10^9$ | | | |
| Tonsils | – | – | – | + | – | + | – | – | 2.1 | 1.9 |
| Retro-pharyngeal ln | – | – | – | – | – | – | 4.0 | 3.0 | 1.8 | NA |
| Bronchial ln | – | – | – | – | – | – | 5.7 | 1.1 | 3.6 | 4.5 |
| Mesenteric ln | – | – | – | – | – | – | 3.7 | 1.1 | 4.3 | 4.1 |
| Ileo-caecal ln | – | + | – | – | – | + | 3.9 | 1.8 | 3.9 | 3.6 |
| Lung | – | – | – | – | – | – | 2.4 | – | 4.8 | 2.0 |
| Lung lesion | – | – | – | – | – | – | 6.4 | – | NA | 2.2 |
| Liver | – | – | – | – | – | – | – | – | 5.5 | 1.4 |

TABLE 3-continued

Organ invasion of wild-type *S. choleraesuis* strain 38 (Scs 38) and its PMNL-adapted derivative (Scs 38 7× PMNL) in pigs. Pigs were fed respective cultures by gavage. All surviving pigs were euthanized two weeks after infection and selected organs were cultured from tenfold dilutions of organ suspensions. The numbers denote $\log_{10}$ of colony forming units. A single colony from the 1:10 (lowest) dilution was noted by "+".

| | Pigs | | | | | | | | | |
|---|---|---|---|---|---|---|---|---|---|---|
| | 1 | 2 | 3 | 4 | 5 | 6 | 7 | 8 | 9 | 10 |
| Inocula | Scs 38 7× PMNL 3.7 × $10^9$ | | | | | | Scs 38 3.2 × $10^9$ | | | |
| Liver lesion | − | − | − | − | − | − | − | − | >6 | NA |
| Spleen | − | − | − | − | − | − | − | − | 5.5 | − |
| Ileum | + | + | − | + | − | − | 1.1 | + | 4.7 | 2.5 |
| Colon | + | − | − | + | − | + | 2.9 died | − | 4.2 died | 1.4 died |

TABLE 4

Effects of wild type *S. dublin* and *S. enteritidis* and of their porcine PMNL-adapted derivates on mice. The PMNL selection process was the same as described for *S. choleraesuis* in Table 1.

| Inocula: | Dose | No Mice | Killed days pi | No Dead | No spleens infected | $Log_{10}$ bacteria/spleen |
|---|---|---|---|---|---|---|
| *S. dublin* | 8.9 × $10^1$ | 10 | 9 | 1 | 10/10 | 7.17 ± 0.28 |
| *S. dublin* 5× PMN | 1.2 × $10^2$ | 10 | 9 | 0 | 3/0 | 5.60 ± 0.22 |
| *S. enteritidis* | 9.6 × $10^1$ | 10 | 9 | 2 | 10/10 | 7.22 ± 0.32 |
| *S. enteritidis* 5× PMN | 1.2 × $10^2$ | 10 | 9 | 0 | 4/10 | 5.01 ± 0.70 |

TABLE 5

Immunizing effect of *S. choleraesuis* strain 38 adapted to porcine PMNLs (Scs 38 7× PMNL or 7× PMNL). Three groups of 10 mice each were given footpad injections of Scs 38 7× PMNL in tenfold incremental doses (left column). Three weeks later, all 3 groups, and an additional challenge control group were given footpad injections of 1.6 × $10^3$ Scs 38. Scs 38 7× PMNL carried a xylose$^+$ marker, and thus enabled the separate identification of spleens and colonies infected with the immunizing strain (right columns).

| Scs injected | | No | Days | No | No spleens infected | | Spleen CFU counts | |
|---|---|---|---|---|---|---|---|---|
| Scs 38 7× PMNL | Scs 38 | mice | pi | dead | Scs 38 | 7× PMNL | $Log_{10}$ Scs 38 | $log_{10}$ 7× PMNL |
| 2.0 × $10^1$ | 1.6 × $10^3$ | 10 | 8 | 2 | 5/8 | 2/8 | 2.90 ± 0.83 | 0.50 ± 0.12 |
| 2.0 × $10^2$ | 1.6 × $10^3$ | 10 | 8 | 0 | 3/10 | 5/10 | 1.40 ± 0.51 | 0.62 ± 0.19 |
| 2.0 × $10^3$ | 1.6 × $10^3$ | 10 | 8 | 0 | 2/10 | 1/10 | 0.82 ± 0.55 | 0.33 NA |
| NA | 1.6 × $10^3$ | 10 | 8 | 4 | 10/10 | NA | 6.09 ± 0.52 | NA |

EXAMPLE 2

Vaccination of Swine with an Attenuated Strain of *Salmonella choleraesuis*

Materials and Methods

Attenuated Scs 38 strains prepared according to the procedure in the above-described example were used in the following experiments. An attenuated Scs 38 strain subjected to PMNL exposure five times was designated Scs 54.

Mouse experiments. Female Swiss Webster mice approximately 6 weeks old were inoculated in the left footpad with either the avirulent or virulent Scs 38 strains at varying dosages. The mice were killed by cervical dislocation 8 or 12 days after inoculation with Salmonella. Their spleens were excised aseptically, homogenized and diluted by serial tenfold dilutions, and each dilution plated on MacConkey agar.

Pig vaccine safety experiment. Ten pigs weighing approximately 20 kg were purchased from an Iowa State University herd with no history of clinical salmonellosis. Rectal samples from these pigs were cultured twice for Salmonellae, and no Salmonellae were recovered. Baseline temperatures were also determined on two occasions prior to the start of the experiment. Five of the pigs were randomly assigned to the vaccine safety test group, and were given 3.7×$10^9$ colony forming units (CFUs) of Scs 54 by gavage. The other five pigs were assigned to the challenge control group and were given 3.2×$10^9$ Scs 38 CFUs by gavage. of the surviving pigs were killed 14 days after Salmonella treatment. Ten organs or lymphoid tissues were cultured quantitatively for Salmonella.

Vaccine Efficacy Experiment 1. This vaccine efficacy experiment consisted of a double blind study involving nursery pigs (barrows and gilts) from an Iowa farm with a history of severe current swine paratyphoid with multiple bacteriologic diagnoses at the time of the start of this experiment. All of the pigs were inoculated by nasopharyngeal gavage. One randomly selected group of 23 pigs was given 2.2×$10^8$ colony forming units (CFU) of Scs 54. A second group of 22 pigs was given 2.2×$10^8$ autoclaved Scs 54. A third group of 22 pigs was given a starch suspension (placebo) adjusted to the same optical density as the Scs suspensions. The groups were identified by ear notching, and all pigs were co-mingled Bottles were labeled "A", "B", and "C" and the ingredient in each bottle was revealed to the owner and attending veterinarian at the conclusion of the experiment only. All of the pigs were examined daily, and were weighed on the day of the trial, and 18 days later.

Vaccine Efficacy Experiment 2. Ten pigs were randomly selected from a group of pigs vaccinated per os with 1.0×$10^9$ CFUs of Scs 54 and were co-mingled with 6 healthy unvaccinated control pigs 20 days after vaccination. All 16 pigs were given 2.0×$10^9$ CFU of a virulent *S choleraesuis* field isolate (challenge) by gavage. For reasons unrelated to salmonellosis, one vaccinated and one control pig were later excluded from the experiment. Rectal temperatures were taken twice before challenge exposure and on days 2, 4, 5, 6, 7, 11, and 13 after challenge. All pigs were weighed two days before challenge exposure and 7 and 14 days after challenge exposure. All challenge control pigs, and 5 randomly selected vaccinated and challenged pigs were killed and necropsied 14 days after challenge exposure. Bacteriologic cultures were done on 6 organs of the challenge control pigs, and on 10 organs of the vaccinated and challenged pigs.

Differences between group means were evaluated by appropriate student t tests, and differences between count data were evaluated by chi-square tests.

Field trials. Scs strain 54 was given to several thousand pigs in drinking water on 8 Iowa Farms with current acute and endemic salmonellosis with multiple bacteriologically confirmed diagnoses. On 2 farms, vaccinated during the summer and fall of 1990, the average concentration of Scs 54 was approximately $10^7$ CFU/-dose, whereas from Dec. 7, 1990 the dose was increased to $10^9$ CFU/dose. On the average, the pigs weighed about 5–6 kgs., thus, the preferred dose to be administered is about $10^7$–$10^9$ bacteria/Kg of body weight.

Results

Mouse virulence experiments. Increased numbers of virulent Scs 38 caused increased mortality and spleen infections in mice; however, spleen CFUs remained relatively constant at $10^6$ and were dose independent. See Table 6. By contrast, Scs 38 exposed once to neutrophils (Scs 38 PMNa-1×) caused no mortality and reduced spleen colonization, as well as having a tenfold reduction of splenic CFUs. When Scs 38 was exposed five times to neutrophils (Scs38 PMNa-5×), it had almost totally lost virulence and invasiveness. Similar loss of lethality, virulence and invasiveness was achieved by adapting Scs 38 to lysosomal extracts (PMNlys-13×) of porcine neutrophils. See Table 6.

Mouse immunization experiments. Three groups of 10 mice were each injected with 10-fold increments of Scs 54 (38PMNa-5×); 21 days later they, and a control group of 10 mice, were injected with $1.6\times10^3$ virulent Scs 38. See Table 7. Protection from challenge, judged by reduced mortality and spleen colonization was obtained in a dose-dependent fashion, i.e., when mice were immunized with $2.0\times10^3$ Scs 54, none died after challenge and only 2 of 10 had spleens colonized with the challenge strain at very low level (0.82 $\log_{10}$ CFUs). The count data i.e., deaths and number of spleens colonized, were significantly different between groups of mice immunized with $2.0\times10^2$ or higher Scs 54 and challenge control groups ($p<0.001$).

Pig vaccine safety experiment. When the neutrophil adapted mouse avirulent Scs 54 was given to five pigs, a mild temperature rise occurred on day 4 p.i. Five pigs were given a similar dose of the virulent Scs 38 parent strain and had highly elevated temperatures from p.i. days 2 through 8 and 3 of the 5 pigs died during this period. See FIG. 1. All of the pigs given the avirulent Scs 54 strain remained in good health and were killed 14 days after treatment. Only a few colonies of Scs 54 were isolated from the tonsils, ileocecal lymph nodes, ileum and colon of a few of these pigs, i.e., 7/50 organ suspensions (14%) yielded a few colonies from the undiluted organ suspensions. See Table 8. By contrast, 3 of the 5 pigs infected with the virulent Scs 38 strain had high bacterial counts in multiple organs and died, while the 2 remaining controls were moderately infected. See Table 8. The number of organs infected in the control group of pigs was 33/49 (67%).

Pig vaccine efficacy experiment 1. The pigs given $2.2\times10^8$ Scs 54 gained an average daily weight of at least 100 g in excess to pigs in either of the two control groups. There were no death losses among vaccinated pigs and none of the 23 vaccinated pigs required parenteral antibiotic treatment during the 18 day observation period. One pig died of salmonellosis in each of the 2 control groups of 22 pigs, and 3 pigs required parenteral treatment of gentamicin for acute septicemic salmonellosis during the observation period. See Table 9.

Figure 2:
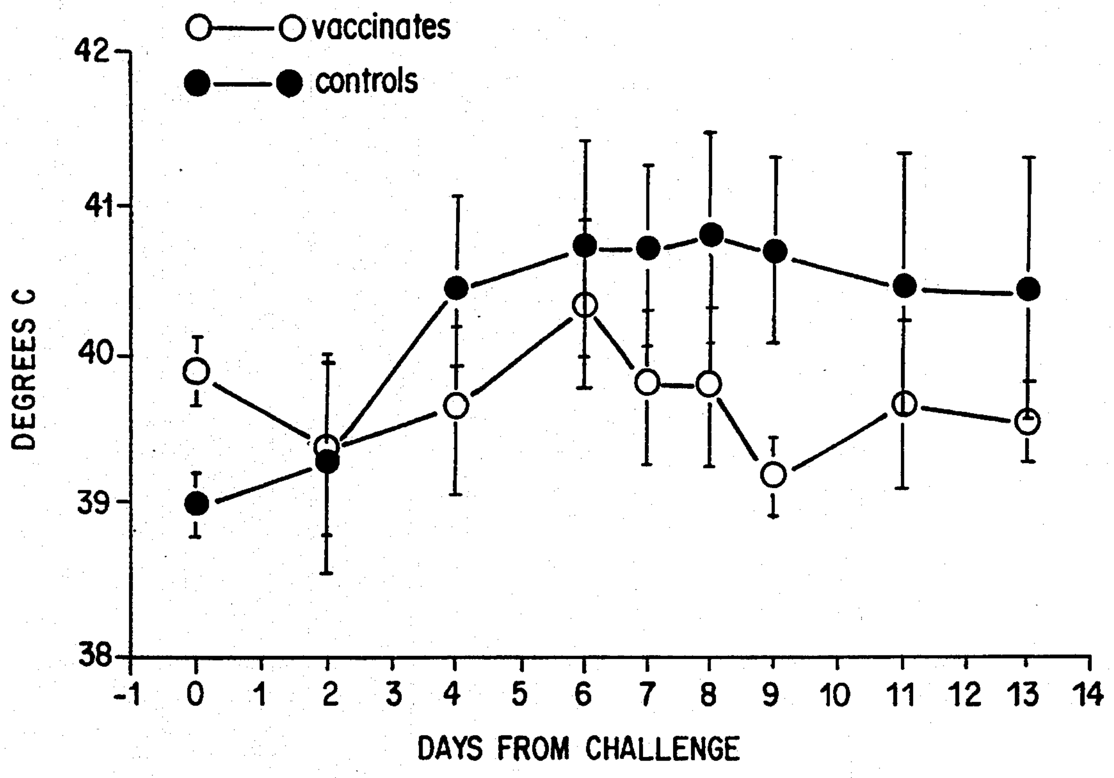
FIG. 2 is a graphic representation of the daily rectal temperatures of 9 pigs vaccinated with live *S. choleraesuis* strain 54 per os and challenged with a virulent field strain of *S. choleraesuis* and of 6 challenge control pigs. All pigs were challenged with $10^9$ CFUs per os.
Figure 3:
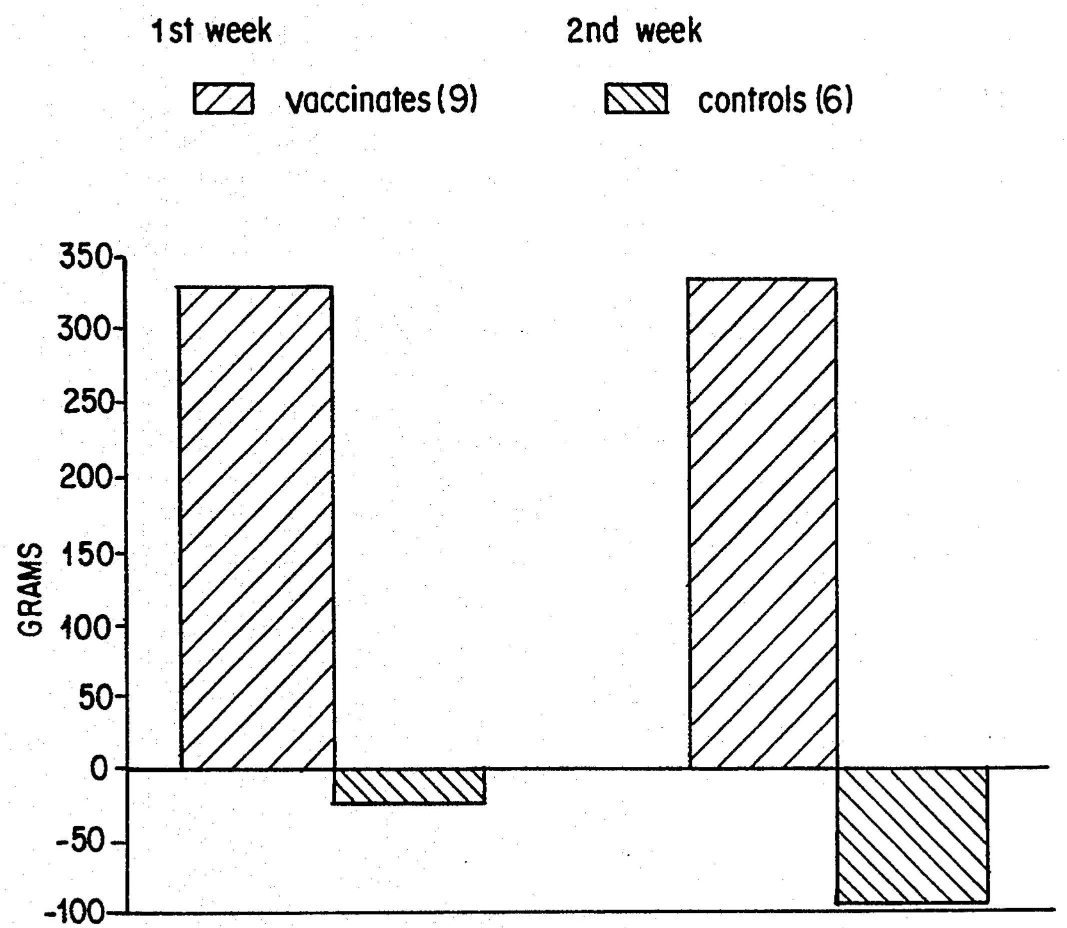
FIG. 3 is a graphic representation of the daily weight changes of 9 pigs vaccinated with *S. choleraesuis* strain Scs 54 and of 6 challenge control pigs after challenge with a virulent field strain. Weight changes between vaccinated and challenge control pigs were significantly different one week as well as two weeks after challenge ($P<0.01$) by $x^2$.

Pig vaccine efficacy experiment 2. The vaccinated pigs challenged with $2.0\times10^9$ virulent *S. choleresuis* field strain had a single rectal temperature rise to 40.4° C. 6 days after challenge. The temperature rise subsided on the next day. The challenge control pigs had a sustained temperature rise to 40.6° C. and higher from 5 to 13 days after vaccination. Three of these pigs died during the 14 day observation period. See FIG. 2. The average daily weight gains of vaccinated and challenged pigs were 331 g, while the challenge control pigs lost weight during the first week after challenge. The corresponding values for the second week were 344 g for the vaccinated and challenged group and −54 g for the challenge control group. See FIG. 3. Rectal temperature differences between the 2 groups from day 5 to 13 and weight differences for the 2-week observation were significantly different ($p<0.01$). The challenge virulent *S. choeraesuis* field strain was isolated from the lungs, spleens, kidneys and mesenteric lymph nodes of all challenge control pigs. See Table 10. All spleen, kidney, ileum, ileocecal lymph node, colon and colonic lymph node cultures were negative for Salmonella in the vaccinated and challenged group of pigs. Overall, 28/30 organs (93%) from the challenge control group, and 7/50 organs (14%) from the vaccinated and challenged group yielded Salmonella. See Table 10. This organ count difference was significant at $p<0.01$.

Field trials. On the farms with endemic salmonellosis when Scs 54 was given in the drinking water at a concentration of $10^7$ CFU/dose, salmonellosis occurred several weeks after vaccination. When the concentration of Scs 54 was raised to $10^9$ CFU/dose, no further outbreaks of salmonellosis have occurred. In one instance, 150 pigs were given the vaccine in the drinking water at $10^9$ CFUs/dose in the face of an outbreak. Six pigs have died of salmonellosis on the days immediately preceding and 2 days following vaccination. The diagnosis was confirmed by Salmonella cultures from the lungs, livers, and lymph nodes of 3 dead pigs. Fifteen pigs had rectal temperatures between 40° and 42° C. two and three days after vaccination. There were no further losses or clinical signs of salmonellosis in this group of pigs from the 4th day after vaccination in the drinking water. There were no clinical, pathological or microbiological diagnoses of salmonellosis made on the 8 farms for the last 6 months since vaccination in the drinking water at a concentration of $10^9$ CFU/dose was implemented. These observations suggest that Scs 54 is effective and stable under field conditions, and does not revert to virulence.

Discussion

Observations with Scs 54 indicate that oral immunization of swine with this strain is very effective, and that the loss of the 50 kb plasmid did not prevent excellent immunogenicity in mice when vaccinated and challenged parenterally and in pigs vaccinated and challenged per os. While the mechanism(s) of immunogenicity of Scs 54 are unknown at the present time, the strain appears to be preferentially adapted to life within neutrophils. *Salmonella choleraesuis* strain 54 has effectively stopped salmonellosis in field trials involving 8 large swine herds and several thousand pigs with no reversion to virulence when the vaccine was given per os at a dose of $10^9$ CFU.

TABLE 6

Virulence of *S. choleraesuis* 38 and porcine neutrophil adapted derivatives in Swiss Webster mice. Data were pooled from 4 experiments.

| Inocula | Dose | No Mice | % Dead | % spleens infected | $Log_{10}$ Scs 38/ spleen |
|---|---|---|---|---|---|
| Scs 38 | $1.6\text{–}5.0 \times 10^1$ | 27 | 11 | 85 | $6.96 \pm 1.12$ |
| | $1.6\text{–}5.0 \times 10^2$ | 35 | 20 | 91 | $6.10 \pm 0.92$ |
| | $1.6 \times 10^2$ | 10 | 40 | 100 | $6.09 \pm 0.40$ |
| Scs 38 PMNa-1× | $4.610^2$ | 17 | 0 | 35 | $5.22 \pm 0.52$ |
| Scs 38 | $4.7\text{–}6.4 \times 10^1$ | 33 | 0 | 9 | $0.30 \pm 0.19$ |
| PMNa-5× | $4.3 \times 10^3$ | 20 | 0 | 0 | 0.00 |
| Scs 38 | $2.8 \times 10^1$ | 16 | 0 | 0 | 0.00 |
| PMNlys-13× | $6.5 \times 10^2$ | 8 | 0 | 12 | 3.00 |
| | $2.5 \times 10^3$ | 5 | 0 | 0 | 0.00 |
| | $2.5 \times 10^4$ | 5 | 0 | 0 | 0.00 |
| | $2.5 \times 10^5$ | 5 | 0 | 0 | 0.00 |

TABLE 7

Immunizing effect of porcine neutrophil adapted *S. choleraesuis* strain 54

| Salmonella injected* | | No | Days | No | No spleens | Spleen CFU $Log_{10}$ |
|---|---|---|---|---|---|---|
| Scs 54 | Scs 38 | mice | pi | dead | infected | Scs 38 |
| $2.0 \times 10^1$ | $1.6 \times 10^3$ | 10 | 8 | 2 | 5/8 | $2.90 \pm 0.83$ |
| $2.0 \times 10^2$ | $1.6 \times 10^3$ | 10 | 8 | 0 | 3/10 | $1.04 \pm 0.51$ |
| $2.0 \times 10^3$ | $1.6 \times 10^3$ | 10 | 8 | 0 | 2/10 | $0.82 \pm 0.55$ |
| NA | $1.6 \times 10^3$ | 10 | 8 | 4 | 10/10 | $6.09 \pm 0.52$ |

*Swiss Webster mice were first injected with Scs 54, and 21 days later with the virulent challenge strain Scs 38. All live mice were killed on day 8 p.i.

TABLE 8

Quantitative isolation of PMNL-adapted *S choleraesuis* (Scs 54) and of virulent Scs 38 from organs of pigs two weeks after infection by gavage.

| | Pigs | | | | | | | | | |
|---|---|---|---|---|---|---|---|---|---|---|
| | 1 | 2 | 3 | 4 | 5 | 6 | 7 | 8 | 9 | 10 |
| Organs | Scs 54 $3.7 \times 10^9$ | | | | | | Scs 38 $3.2 \times 10^9$ | | | |
| Tonsils | − | − | − | +* | − | + | − | − | 2.1 | 1.9 |
| Retro-pharyngeal ln | − | − | − | − | − | − | 4.0 | 3.0 | 1.8 | ND |
| Bronchial ln | − | − | − | − | − | − | 5.7 | 1.1 | 3.6 | 4.5 |
| Mesenteric ln | − | − | − | − | − | − | 3.7 | 1.1 | 4.3 | 4.1 |
| Ileo-caecal ln | − | + | − | − | − | + | 3.9 | 1.8 | 3.9 | 3.6 |
| Lung | − | − | − | − | − | − | 6.4 | − | 4.8 | 2.1 |

TABLE 8-continued

Quantitative isolation of PMNL-adapted *S choleraesuis* (Scs 54) and of virulent Scs 38 from organs of pigs two weeks after infection by gavage.

| | Pigs | | | | | | | | | |
|---|---|---|---|---|---|---|---|---|---|---|
| | 1 | 2 | 3 | 4 | 5 | 6 | 7 | 8 | 9 | 10 |
| Organs | Scs 54 $3.7 \times 10^9$ | | | | | | Scs 38 $3.2 \times 10^9$ | | | |
| Liver | − | − | − | − | − | − | − | − | 5.5 | 1.4 |
| Spleen | − | − | − | − | − | − | − | − | 5.5 | − |
| Ileum | + | + | − | + | − | − | 1.1 | + | 4.7 | 2.5 |
| Colon | + | − | − | + | − | + | 2.9 | − | 4.2 | 1.4 |
| | | | | | | | died | | died | died |

*A few Salmonella colonies from the undiluted organ suspension.
$Log_{10}$ of CFUs/g tissue from tenfold dilutions.

TABLE 9

Clinical Observations of pigs given $2.2 \times 10^8$ *Salmonella choleraesuis* strain Scs 54 per os, and 2 control groups

| Experimental Group | Daily weight gain (g) | Deaths | Gentamicin* treatment for Salmonellosis |
|---|---|---|---|
| Vaccinates (Scs 54) N = 23 | 593 | 0 | 0 |
| Controls (Autoclaved Scs) N = 22 | 488 | 3 | 11 |
| Controls (starch) N = 22 | 453 | 2 | 9 |

*Pigs required 3-day intramuscular gentamicin treatment for salmonella septicemia.

TABLE 10

Organ cultures from pigs vaccinated with Scs 54 and challenged with $2.0 \times 10^8$ virulent *S choleraesuis*, and from challenge control pigs

| | Pig Groups | | | | | | | | | |
|---|---|---|---|---|---|---|---|---|---|---|
| | Vaccinates | | | | | Challenge Controls | | | | |
| Pig Nos: | 402 | 404 | 407 | 410 | 412 | 414 | 415* | 417* | 418 | 419* |
| Organs | | | | | | | | | | |
| Lung | Neg | Neg | Neg | Neg | Pos | Pos | Pos | Pos | Pos | Pos |
| Liver | Pos | Neg | Neg | Neg | Pos | Neg | Pos | Pos | Neg | Pos |
| Spleen | Neg | Neg | Neg | Neg | Neg | Pos | Pos | Pos | Pos | Pos |
| Kidney | Neg | Neg | Neg | Neg | Neg | Pos | Pos | Pos | Pos | Pos |
| Ileocec ln | Neg | Neg | Neg | Neg | Neg | ND | ND | ND | ND | ND |
| Jejunal ln | Pos | Pos | Neg | Neg | Pos | Pos | Pos | Pos | Pos | Pos |
| Colonic ln | Neg | Neg | Neg | Neg | Neg | ND | ND | ND | ND | ND |
| Ileocec valve | Pos | Neg | Neg | Neg | Neg | Pos | Pos | Pos | Pos | Pos |
| Ileum | Neg | Neg | Neg | Neg | Neg | ND | ND | ND | ND | ND |
| Colon | Neg | Neg | Neg | Neg | Neg | ND | ND | ND | ND | ND |
| Ratio: organs infected/total sampled | 7/50 (14%) | | | | | 28/30 (93%) | | | | |

*Pigs died of salmonellosis. ND = not done. ln = lymph node

EXAMPLE 3

Characterization of an *Salmonella Choleraesuis* Isolate Following Repeated Neutrophil Exposure The purpose of this investigation was to determine the changes associated with Salmonella virulence following exposure to porcine neutrophils. Strain 38 was used in this investigation because of its virulence, and ability to ferment glycerol (+) which was used as a marker for recovery. This has been evaluated by measuring virulence in a mouse model, resistance to phagocyte killing., plasmid analysis and invasion.

Materials and Methods

Bacterial strains and cultures. Bacterial isolates were grown on MacConkey agar (Difco Laboratories, Detroit, Mich.) and pure cultures isolated. Cultures were stored on trypticase soy agar (TSA) (Difco) soft agar slants at room temperature, and in trypticase soy broth (TSB) (Difco) which contained 15% glycerol at −70° C. Routine growth of bacterial isolates was performed on TSA at 37° C. for 12 h. Bacterial strains *E. coli* MC1040-2 and LE392 were propagated in Luria broth or in some cases in super broth (32 g tryptone, 20 g yeast extract, 5 g sodium chloride per liter). Descriptions of genotypes are presented in Table 11.

Cell culture. Vero cells were obtained from the National Veterinary Services Laboratory U.S.D.A. The Vero cells were grown in Dulbecco's minimum essential media (DMEM) (Sigma Chemical Co., St. Louis, Mo.) with 10% fetal calf serum (Hyclone Laboratories Inc., Logan, Utah), at 37° C. with 5% $CO_2$ until confluent.

Neutrophil isolation. Porcine neutrophils were obtained from freshly collected, anticoagulated blood from normal pigs. The neutrophils were isolated using a Percoll gradient procedure as previously described. See Roof et al., *Vet. Immuno. Immunopathol,* 23:365–376 (1988) which is incorporated in its entirety by reference.

Neutrophil passage of *S. Choleraesuis.* An overnight culture of *S. choleraesuis* 38 grown on MacConkey agar was exposed to isolated porcine neutrophils in a bactericidal assay as previously described. See Roof et al., *Vet. Immunol. Immunopathol.,* 23:365–376 (1989). Opsonized *S. choleraesuis* were incubated in M199 (Sigma) with neutrophils for 30 min to allow ingestion. Gentamicin (100 ug/ml) and kanamycin (100 ug/ml) were added for one hour to kill all extracellular bacteria. The neutrophils were allowed to settle and the supernatant was sampled to insure killing of extracellular Salmonella. A separate sample of *S. choleraesuis* without neutrophils was also exposed to antibiotics to measure killing. The neutrophils were washed three times with phosphate buffered saline (PBS; 0.15M NaCl in 0.015M phosphate buffer, pH 7.4), and resuspended to their initial volume. A 100 ul aliquot was removed and lysed with distilled water to release intracellular bacteria. This sample was then diluted and plated on MacConkey media and grown overnight at 37° C. Individual colonies were selected and resuspended to $2\times10^8$ colony forming units (CFU)/ml. This procedure was repeated five times to enrich for a population of neutrophil-resistant *S. choleraesuis.* After the fifth passage, a single glycerol (+) clone was selected for observation and designated *S. choleraesuis* 38 PMNa-5×.

Mouse infection with *S. choleraesuis.* Bacteria were suspended to $2\times10^8$ CFU/ml in PBS and tenfold dilutions from $10^1$ to $10^5$ CFU/ml were injected intraperitoneal (i.p.) into Balb/c mice as described. See Dulbecco, *Microbiology,* pg. 791 (1990), which is incorporated herein in its entirety by reference.

*S. Kholeraesuis* susceptibility to neutrophil killing. The susceptibility of *S. choleraesuis* 38 and 38 PMNa-5× to neutrophil killing was assessed by two methods: 1) A modification of a colorimetric assay that measured the ability of live bacteria to reduce 3-[4,5-dimethylthiazol-2-yl]-2,5-diphenytetrazolium bromide (MTT) to purple formazan was employed. See Stevens et al., *Vet. Immunol. Immunopthol.,* 27:accepted (1991), which is incorporated herein in its entirety by reference. Opsonized *S. choleraesuis* ($2\times10^8$/ml) in RPMl 1 1640 (Sigma) with 10% FCS (Hyclone) was incubated for 1 h with $1\times10^7$ neutrophils/ml. Following incubation, 0.2% Saponin was added to lyse the neutrophils. The remaining live *S. choleraesuis* were allowed to reduce MTT and then compared to a standard curve to determine the numbers of viable *S. choleraesuis.* 2) A hydrogen peroxide sensitivity test was performed comparing the viability of *S. choleraesuis* 38 and PMNa-5× after exposure to 60 mM hydrogen peroxide for 1 hour. See Christman et al., *Cell,* 41:753–762 (1985), which is incorporated herein in its entirety by reference.

Determination of Salmonella invasion of Vero Cells. The invasion assay was performed in eight well plates as previously described. See Roof et al., *Vet. Microbiol.,* accepted 1991, which is incorporated herein in its entirety by reference. Briefly, freshly prepared Salmonellae (500 ul) were added to each well in a ratio of 1000:1 bacteria ($2\times10^8$) to Vero cells ($2\times10^5$). After incubation for 2 hours, the wells were washed 3 times with DMEM containing 100 ug/ml gentamicin to kill all extracellular bacteria. Controls containing bacteria only were performed at the same time to measure the killing of extracellular bacteria. The wells were incubated for an additional 2 hours with DMEM containing gentamicin. The supernatants were examined for sterility by plating onto brain heart infusion agar (BHI) (Difco). The wells were washed an additional 3 times with DMEM to remove gentamicin, and the cell monolayers were lysed using 0.1% sodium dodecyl sulfate, releasing all intracellular bacteria. Samples from each well were then diluted in PBS and plated in quadruplicate to determine the CFU. Results were expressed as the mean and standard error of the mean of five experiments.

Plasmid analysis. Plasmid DNA was isolated by an alkaline lysis method (1) from overnight cultures grown in super broth and purified by an ethidium bromide-cesium chloride gradient as previously described. See Sawbrook et al., Molecular Cloning: A Laboratory Manual, (1989), which is incorporated herein in its entirety by reference. Plasmid analysis was performed using a 0.5% agarose gel in Tris-borate buffer, run for 4 hours at 70 mV and stained with ethidium bromide. Southern blots were performed using nylon membranes (Schleicher & Schuell Inc., Keene, N.H.) and standard methodology. The 50 kilobase plasmid of *S. choleraesuis* was excised from the gel, isolated using Geneclean II (Bio101 Inc., La Jolla, Calif.), and labeled with $^{32}P$ using oligonucleotide labeling (Amersham Corp., Arlington Heights, Ill.).

The introduction of the 50 kb plasmid into the cured strain 38 PMNa-5× was accomplished by labeling the plasmid from strain 38 with mini-Mu, transforming into the recipient and selecting for kanamycin resistance. See Groisman et al., *J. Bacteriol.,* 168:357–364 (1986), which is incorporated herein in its entirety by reference.

Lysates of mini-Mu phage were prepared by thermoinduction of MC1040-2 which contained mini-Mu as a plasmid replicon and also Mucts62 temperature-sensitive helper phage in the chromosome. Infections were performed by mixing dilutions of phage with mid-log phase culture of strain 38. Following a 2 hour incubation, cells were plated on kanamycin (10 ug/ml) containing agar. Resistant colonies were collected in bulk and grown overnight in super broth at 37° C. and the plasmid DNA prepared as described above. The plasmid was isolated by electroelution from agarose slices using an Elutrap (Schleicher & Schuell) run at 200 mV for 18 hours. Strain 38 PMNa-5× was electroporated with this plasmid preparation, using a BTX 100 power supply (San Diego, Calif.) at 725 mV for 5 msec and an electrode gap of 0.5 mm. The bacteria were then plated on kanamycin agar. Plasmid DNA was isolated from kanamycin resistant colonies, and analyzed by DNA-DNA hybridization as described above.

Complement sensitivity. Normal porcine and guinea pig sera were obtained by venipuncture, aliquoted and stored at −20° C. These sera did not agglutinate Salmonella O and H antigens. The complement assay was conducted as described elsewhere. See Moll et al., *FEMS Microbiol. Lett.*, 6:273–276 (1979), which is incorporated herein in its entirety by reference. Briefly, overnight cultures of Salmonella were diluted 1:100 in TSB and incubated at 37° C. until they reached an O.D. of 0.20 at 540 nm ($2\times10^8$ cfu/ml.). The bacteria were then centrifuged at 5000×g for 10 min and resuspended in PBS. Bacteria (500 ul) were then added to 2 ml of PBS containing serum at concentrations ranging from 10–50%. The bacterial suspensions were then incubated at 37° C. and samples taken at 0 and 90 min, diluted in PBS, and plated on MacConkey agar for viable counts.

Carbohydrate and enzymatic activity. *S. choleraesuis* strain 38 and 38 PMNA-5× were examined by API-CHE for fermentation of 49 substrates, and for 19 enzyme activities by API-ZYME (API Analytab Prod., Plainview, N.Y.).

Statistical analysis. Data were analyzed by the Student's t test as previously described. See Zar, J. H., *Biostatistical Analysis*, (1984), which is incorporated herein in its entirety by reference. All experiments were carried out in at least triplicate with reproducible results.

Results

*S. choleraesuis* virulence for mice. The parent strain 38 was virulent in Swiss-Webster and Balb/c mice by footpad and i.p. injection with an $LD_{50}$ of $10^{2.84}$ in Swiss-Webster mice. The PMN-adapted derivative, 38 PMNa-5× had a $LD_{50}$ of greater than $10^5$ in mice. The pathogenicity of Salmonella for mice was evaluated based on death, spleen infection and number of recovered bacteria. The parent strain 38 caused 100% death, 100% spleen infection, and $Log_{10}8.4$ bacteria per spleen, but strain 38 PMNa-5× failed to infect spleens or kill mice. See Table 12. Strain 38 PMNa-5× had been cured of a 50 kb plasmid, and following re-insertion of a kanamycin-marked plasmid, virulence was partially restored. Death rates of the resulting strains (38-K28, 38-K65, and 38-K71) ranged from 16–66% with 100% infection of spleens and bacterial recovery intermediate between strain 38 and 38 PMNa-5×. See Table 12.

Viability of *S. choleraesuis* 38 and 38 PMNa-5× following PMN and hydrogen peroxide exposure. The overall viability of these two isolates following neutrophil exposure and ingestion was determined colorimetrically by measuring the reduction of MTT to formazan. The parent isolate 38 remained 32% viable after 1 hour of neutrophil exposure compared to 56% viability for the 38 PMNa-5× isolate. See Table 13. Strains 38-K28, K65, and K71 were intermediate in resistance to neutrophil killing. See Table 13. Viability was also examined after exposure to hydrogen peroxide. *S. choleraesuis* was exposed to 60 mM hydrogen peroxide for 1 hour and then viable numbers of bacteria determined by plating and counting CFU. The parent isolate 38 remained 50% viable after one hour compared to 65% viable for the PMN adapted 38 PMNa-5×. See Table 13. Strains 38-K28, K65, and K71 were intermediate in susceptibility to hydrogen peroxide killing. See Table 13.

DNA analysis. Plasmid DNA was isolated from *S. choleraesuis* before and after neutrophil passage. Following the PMN-adaptation process, the isolate was cured of its large virulence plasmid. This was confirmed by DNA-DNA hybridization using a $^{32}P$-labeled virulence plasmid from the parent strain as a specific probe. To determine the role of the virulence plasmid in the phenotypic changes noted following neutrophil-adaptation, strain 38 PMNa-5× was re-introduced with a 50 kb plasmid from the parent strain. This was accomplished by marking the parent plasmid with a Mu derivative coding for kanamycin resistance. See Groisman et al., *J. Bacteriol.*, 168:357–364 (1986). The marked plasmid was introduced by electroporation and presence of the plasmid was confirmed by DNA-DNA hybridization. Thirteen kanamycin resistant derivatives (K-strains) of strain 38 PMNa-5× were isolated by mini-Mu transfection and placed into mice to study their virulence potential. Of these, three were recovered from mice after 14 days, 38-K28, 38-K65, and 38-K71. These three strains displayed intermediate virulence between the parent strain and the neutrophil adapted strain 38 PMNa-5× using mortality, spleen invasion, and the number of recovered bacteria as the criteria for virulence. See Table 12. They were recovered from 100% of the mouse spleens in intermediate numbers, and had death rates ranging from 16–66%. See Table 12. In these strains, the plasmid was stably maintained during the in vivo passage.

Invasion of Vero cell monolayers by *S. choleraesuis* 38 and 38 PMNa-5×. To determine the invasiveness of these isolates, confluent Vero cell monolayers were incubated with live *S. choleraesuis* as previously described. *S. choleraesuis* 38 were recovered at a rate significantly higher than 38 PMNa-5× (3.8 vs 1.1). See Table 13. Strains 38-K28, 38-K65, and 38-K71 had their invasive capabilities restored by the re-introduction of the 50 kb plasmid. See Table 13.

Complement sensitivity. Both isolates were resistant to 50% fresh normal porcine and guinea pig sera. No difference could be noted by optical density of growth or recovery of CFU/ml from the serum sample. The parent strain was 95±3.0% viable and the attenuated 38 PMNa-5× was 96±2.2% viable after 90 min of serum exposure.

Carbohydrate and enzymatic activity. Carbohydrate utilization was examined by the API-CHE system for enteric bacteria. Forty-nine carbohydrates were examined and both isolates fermented the same fifteen of forty-nine samples. One of the fifteen carbohydrates fermented by both 38 and 38 PMNa-5× was glycerol. Glycerol is not typically fermented by *S. choleraesuis* and allowed differentiation from all other laboratory and field isolates examined. Investigations defining typical *S. choleraesuis* fermentation patterns report no (0% glycerol fermentation. See Ewing, W. H., *Enterobacteriaceae* (1986), which is incorporated herein in its entirety by reference. The API-CHE (API Analytab Prod., Plainview, N.Y.) also indicated no (negative (−)) glycerol fermentation by *S. choleraesuis* in their standard identification profile. This allowed glycerol fermentation to be used as an identification marker. Strain 38 PMNa-5× was serologically and biochemically identical to the parental strain 38, and was distinctly different from all other isolates of *S. choleraesuis* examined. Examination of glycerol negative isolates found conversion to glycerol positive to be less than one in $10^8$ CFU/ml. Enzymatic activity was examined using the API-ZYME system with both isolates positive for the same 5 of 19 substrates (alkaline phosphatase, esterase-lipase, leucine amino-peptidase, acid phosphatases, and phosphohydrolase). Both strain 38 and strain 38 PMNa-5× had API-E identification No. 4504510.

Discussion

The pathogenesis of *S. choleraesuis* depends on its ability to invade the intestinal epithelium, survive the host immune response, and then disseminate in the host. The ability of Salmonella to resist phagocyte killing has been well documented, but only recently has the role of environmental induction of bacterial determinants been investigated.

The hypothesis of this research was that during infection, *S. choleraesuis* are repeatedly exposed to ingestion and killing by host phagocytes. During this process, intracellular environmental stimuli from the phagocytes might induce genetic or phenotypic changes in the viable *S. choleraesuis*. Our goal was to mimic these conditions in vitro and identify changes associated with porcine neutrophil association.

Following neutrophil exposure, isolates had increased resistance to killing by neutrophils as well as resistance to hydrogen peroxide. This may have been due to selection for isolates which constituitively express resistance proteins, similar to OxyR and phoP as described with *S. typhimurium*. See Storz et al., *Science*, 248:189-194 (1990), Fields et al., *Science*, 243:1059-1062 (1989) and Groisman et al., *Proc. Natl. Acad. USA*, 86:7077-7081 (1989), all of which are incorporated herein in their entirety by reference.

The loss of virulence in these isolates for mice was unexpected. One possible explanation may be the loss of the *S. choleraesuis* 50 kb plasmid previously shown to be involved in the invasion process and virulence. See Gulig et al., *Infect. Immun.*, 55:2891-2901 (1987), which is incorporated herein in its entirety by reference. Our data support this conclusion since the re-introduction and stable maintenance of the plasmid resulted in partial restoration of virulence. See Table 12. Because full virulence was not restored, other genetic changes may have also occurred in the neutrophil-adapted strain. This may correlate with induction of stress- or heat-shock proteins beneficial for survival inside neutrophils, but this study did not address this possibility. Sixteen of 19 K-strains did not maintain the virulence plasmid in-vitro and subsequently were not recovered from mice. This suggests that a genetic lesion(s) had occurred in the neutrophil-adapted strain in a gene(s) involved in plasmid replication. The stable K-strains would thus contain revertants or suppressor mutations that support maintenance of the virulence plasmid. Since, total virulence was not restored, other undefined changes also may have occurred in the neutrophil adapted strain.

In conclusion, the following changes were noted in *S. choleraesuis* following repeated PMN exposure: 1) There was an overall increased resistance to neutrophil killing and killing by hydrogen peroxide, 2) the neutrophil adapted *S. choleraesuis* lost the large virulence plasmid, 3) the virulence of the neutrophil adapted isolate (38 PMNa-5×) for mice was decreased, 4) *S. choleraesuis* 38 PMNa-5× was non-invasive in a Vero cell assay, and 5) partial restoration of *S. choleraesuis* 38 PMNa-5× virulence and invasiveness was obtained by re-insertion of the 50 Kb plasmid.

TABLE 11

| | Bacterial strains | |
|---|---|---|
| Strain | Description | Source or reference |
| 38 | *S. choleraesuis* wild type (glycerol +) | 1, 7, 20, 28, 29 |
| 38PMNa-5× | *S. choleraesuis* neutrophil adapted 5 passages (glycerol +) | this work |
| 38-K28 | *S. choleraesuis* 38PMNa-5× mini-Mu ($Km^r$) marked plasmid | this work |
| 38-K65 | *S. choleraesuis* 38PMNa-5× mini-Mu ($Km^r$) marked plasmid | this work |
| 38-K71 | *S. choleraesuis* 38PMNa-5× mini-Mu ($Km^r$) marked plasmid | this work |
| $X^{3246}$ | *S. choleraesuis* wild type | Dr. Roy Curtis |
| MC1040-2 | *E. coli* $F^-$ araD169 araB::Mu cts lacX74 galU galK rpsL, pEG5005 | 21 |
| LE392 | *E. coli* $F^-$ hsdR514 ($r_k$−, $m_k$) lacY1 supE44 galT22 trpR55 metB1 | F. C. Minion |

TABLE 12

Virulence of *S. choleraesuis* 38 and 38PMNa-5× in Balb/c mice following intraperitoneal injection of $10^2$ bacteria for 14 days.

| INOCULUM | # OF BACTERIA | # MICE | % DEATH | % INFECTION | $LOG_{10}$ CFU/SPLEEN |
|---|---|---|---|---|---|
| 38 | $1.8 \times 10^2$ | 6 | 100 | 100 | 8.4 |
| 38PMNa-5× | $2.1 \times 10^2$ | 12 | 0 | 0 | 0 |
| 38-K28 | $2.5 \times 10^2$ | 6 | 66 | 100 | 4.4 |
| 38-K65 | $4.5 \times 10^2$ | 6 | 16 | 100 | 4.1 |
| 38-K71 | $3.8 \times 10^2$ | 6 | 50 | 100 | 4.2 |

TABLE 13

Comparison of *S. choleraesuis* and their resistance to neutrophil killing, hydrogen peroxide, and Vero cell invasion.

| Strain | MTT* (%) Survival | $H_2O_2$# (% Survival) | VERO CELL INVASION ($Log_{10}$ cfu/ml) |
|---|---|---|---|
| 38 | 32.1 +/− 2.1§ | 50.5 +/− 0.8 | 3.8 +/− 0.4 |
| 38PMNa-5× | 56.2 +/− 2.9§ | 65.2 +/− 2/2 | 1.1 +/− 0.8 |
| 38-K28 | 49.1 +/− 6.3 | 60.7 +/− 3.7 | 3.5 +/− 0.9 |
| 38-K65 | 48.7 +/− 5.5 | 58.6 +/− 4.1 | 3.5 +/− 1.1 |

TABLE 13-continued

Comparison of *S. choleraesuis* and their resistance to neutrophil killing, hydrogen peroxide, and Vero cell invasion.

| Strain | MTT* (%) Survival | $H_2O_2$# (% Survival) | VERO CELL INVASION ($Log_{10}$ cfu/ml) |
|---|---|---|---|
| 38-K71 | 40.3 +/− 4.2 | 55.0 +/− 2.9 | 3.1 +/− 0.6 |

(*) *S. choleraesuis* strains were evaluated for their resistance to neutrophil killing after 1 h as measured by reduction of 3-[4,5=dimethylthiazol-2-yl]-2,5-diphenyltetrazolium bromide (MTT).
(#) Isolate viability was examined after exposed to 60 mM hydrogen peroxide for 1 h.
( ) Vero cell invasion was determined by exposing *S. choleraesuis* strains to confluent Vero cell monolayers for 2 h, and killing of extracellular bacteria with gentamicin (100 ug/ml). Viable bacteria were recovered and expressed as Log10 cfu/ml. Data (*, #, ) represents mean +/− sem of five experiments.
($, )-identical letters indicate significant differences ($P < 0.01$) between strains.
( )-this isolate is significantly different ($P < 0.01$) than all other strains.

I claim:

1. A vaccine for inducing an immune response to Salmonella bacteria in a pig comprising *Salmonella choleraesuis* var. *Kunzendorf* strain 38 PMNa, having ATCC accession number 55105, in a pharmaceutically acceptable carrier, wherein said *Salmonella choleraesuis* is in an amount effective to produce an immune response.

2. A method for inducing an immune response to Salmonella bacteria in a pig comprising administering to said pig *Salmonella choleraesuis* var. *Kunzendorf* strain 38 PMNa, having ATCC accession number 55105, wherein said *Salmonella choleraesuis* is in an amount effective to produce an immune response.

3. The method of claim 2 wherein said *Salmonella choleraesuis* is administered in a pharmaceutically acceptable carrier.

4. A method of making a vaccine for inducing an immune response to Salmonella bacteria in a pig comprising mixing *Salmonella choleraesuis* var. *Kunzendorf* strain 38 PMNa, having ATCC accession number 55105, with a pharmaceutically acceptable carrier, wherein said *Salmonella choleraesuis* is in an amount effective to produce an immune response.

* * * * *